US009642372B2

(12) United States Patent
Jackson et al.

(10) Patent No.: US 9,642,372 B2
(45) Date of Patent: May 9, 2017

(54) TRICHODERMA MICROSCLEROTIA AND METHODS OF MAKING

(71) Applicants: The United States of America, as represented by the Secretary of Agriculture, Washington, DC (US); Empresa Brasileira De Pesquisa Agropecuaria-Embrapa, Brasilia (BR)

(72) Inventors: Mark A. Jackson, Peoria, IL (US); Gabriel M. Mascarin, Goiania (BR); Nilce Naomi Kobori, Goiania (BR)

(73) Assignees: The United States of America, as represented by The Secretary of Agriculture, Washington, DC (US); Empresa Brasileira de Pesquisa Agropecuaria, Embrapa (BR)

( * ) Notice: Subject to any disclaimer, the term of this patent is extended or adjusted under 35 U.S.C. 154(b) by 0 days.

(21) Appl. No.: 14/801,998

(22) Filed: Jul. 17, 2015

(65) Prior Publication Data

US 2016/0081351 A1 Mar. 24, 2016

Related U.S. Application Data

(60) Provisional application No. 62/052,209, filed on Sep. 18, 2014.

(51) Int. Cl.

| | |
|---|---|
| *A01N 63/04* | (2006.01) |
| *C05F 11/08* | (2006.01) |
| *C12N 1/04* | (2006.01) |
| *C12N 1/14* | (2006.01) |

(52) U.S. Cl.

CPC .............. *A01N 63/04* (2013.01); *C05F 11/08* (2013.01); *C12N 1/04* (2013.01); *C12N 1/14* (2013.01)

(58) Field of Classification Search

CPC .. A01N 63/00; A01N 2300/00; A01N 43/653; A01N 63/02; A01N 63/04; A01N 43/56; A01N 65/00; A01N 27/00; A01N 43/40; A01N 43/50; A01N 43/88; A01N 47/24; A01N 55/00; A01N 37/50; A01N 43/54; A01N 43/60; A01N 37/46; A01N 25/00; A01N 25/08; A01N 25/24; A01N 25/26; A01N 43/52; A01N 25/12; C12N 15/8282; C12N 15/8279; C12N 1/14; C12N 1/04; C12N 9/0004

See application file for complete search history.

(56) References Cited

U.S. PATENT DOCUMENTS

2005/0276790 A1* 12/2005 Yamashita ............. A01N 63/00 424/93.3

FOREIGN PATENT DOCUMENTS

| | | | |
|---|---|---|---|
| JP | 2002-191359 | A | 7/2007 |
| KR | 10-2014-0083122 | A | 7/2014 |
| WO | 2009-083819 | A1 | 7/2009 |
| WO | 2016-044456 | A1 | 3/2016 |

OTHER PUBLICATIONS

Said, Syahiddin Dahlan, "Spore Production by Bicontrol Agent Trichoderma Harzianum in Submerged Fermentation: Effect of Agitation and Aeration", Jumal Rekayasa Kimia dan Lingkungan,: (2007), 6(2): 71-76.

Jin, et al., "Development of media and automated liquid fermentation methods to produce desiccation-tolerant 3ropagules Trichoderma harzianum," Biological Control, (1996), 7(3): 267-274.

Kobori, Nilce N. et al., "Liquid culture production of microsclerotia and submerge conidia by Trichoderm harzianum active against damping-off disease caused by Thizoctonia solani," Fungal Biology, (Apr. 2005), 119(4) 179-190.

* cited by examiner

*Primary Examiner* — Debbie K Ware

(74) *Attorney, Agent, or Firm* — John D. Fado; Mark D. McNemar

(57) ABSTRACT

Disclosed is an invention that relates to the formation of microsclerotial propagules by mycoparasitic fungi and the use of those microsclerotia for plant disease control. Representative microsclerotia propagules formed are from fungal species *Trichoderma harzianum, Trichoderma lignorum, Trichoderma viridae, Trichoderma reesei, Trichoderma koningii, Trichoderma pseudokoningii, Trichoderma polysporum, Trichoderma hamatum*, and *Trichoderma asperellum*.

13 Claims, 3 Drawing Sheets

TRICHODERMA MICROSCLEROTIA AND METHODS OF MAKING

CROSS-REFERENCE TO RELATED APPLICATION

This present application claims priority under 35 U.S.C. §119(e) to U.S. Provisional Ser. No. 62/052,209, which was filed on Sep. 18, 2014, and is hereby incorporated by reference.

FIELD OF THE INVENTION

The invention relates to the formation of microsclerotial propagules by mycoparasitic fungi and the use of those microsclerotia for plant disease control.

BACKGROUND OF INVENTION

The genus *Trichoderma* is a well-known cosmopolitan soil fungus that has been widely explored as an antagonist of numerous plant pathogenic fungi (Howell C R, 2003. Mechanisms employed by *Trichoderma* species in the biological control of plant diseases: The history and evolution of current concepts. Plant Disease 87:4-10; Harman G E, 2006. Overview of mechanisms and uses of *Trichoderma* spp. *Phytopathology* 96:190-194). Isolates of *Trichoderma* species can be successful in plant disease control due to directly antagonizing pathogen activity and/or inducing host resistance responses (Harman G E, 2000. Myths and dogmas of biocontrol: Changes in perceptions derived from research on *Trichoderma harzianum* T-22. *Plant Disease* 84: 377-393). Furthermore, *Trichoderma*'s function as a plant growth promoter has been reported for some strains after establishment as a non-strict plant symbiont by colonizing the rhizosphere (Harman G E, Howell C R, Viterbo A, Chet I, Lorito M, 2004. *Trichoderma* species—Opportunistic, avirulent plant symbionts. *Nature Reviews Microbiology* 2:43-56; Harman G E, Kubicek P K, 1998. *Trichoderma* and *Gliocladium* Vol 2. Enzymes, biological control and commercial applications. Taylor and Francis, London 1-393). Different modes of action for *Trichoderma* strains employed as biocontrol agents were described: a) rhizosphere competence by colonizing the soil and/or parts of the plant or by competition for nutrients; b) mycoparasitism by producing a wide variety of cell wall degrading enzymes against pathogens; c) antibiosis via production of antimicrobial compounds (volatiles and non-volatiles) that can kill the pathogens; d) growth promotion by improving plant development and e) induction of systemic defensive responses in plants (Harman and Kubicek, 1998, ibid; Harman, 2006, ibid).

Currently, the majority of *Trichoderma* products in the biopesticide marketplace are based on solid substrate-produced aerial conidia. Aerial conidia of *Trichoderma* are produced using solid substrate fermentation on moistened grains and this process takes weeks for production and drying, which consequently increases the production costs (Pandey A, Fernandes M, Larroche C, 2008. Current developments in solid-state fermentation. Springer New York, US, 517p. DOI: 10.1007/978-0-387-75213-6; Ramanujam B, Prasad R D, Rangeswaran R, 2010. Mass production, formulation, quality control and delivery of *Trichoderma* for plant disease management. *The Journal of Plant Protection Sciences* 2(2): 1-8). The production of fungal conidia on moistened grains suffers from numerous constraints including high labor costs, poor quality control, long fermentation times, environmental concerns for workers, and difficulties in scale-up. Liquid culture production methods have been investigated and focused on the production of submerged conidia and chlamydospores of *Trichoderma* (Lewis J A, Papavizas G C, 1983. Production of chlamydospores and conidia by *Trichoderma* spp. in liquid and solid growth media. *Soil Biology and Biochemistry* 15: 351-357; Papavizas G C, Dunn M T, Lewis J A, Beagle-Ristaino J, 1984. Liquid fermentation technology for experimental production of biocontrol fungi. *Phytopathology* 74(10): 1171-1175; Tabachnik M, 1989. Method of growing *Trichoderma*. U.S. Pat. No. 4,837,155A; Harman G E, Jin X, Stasz T E, Peruzzotti G, Leopold A C, Taylor A G, 1991. Production of conidial biomass of *Trichoderma harzianum* for biological control. *Biological Control* 1: 23-28; Jin X, Taylor A G, Harman G E, 1996. Development of media and automated liquid fermentation methods to produce desiccation-tolerant propagules of *Trichoderma harzianum*. *Biological Control* 7: 267-274; Sriram S, Roopa K P, Savitha M J, 2011. Extended shelf-life of liquid fermentation derived talc formulations of *Trichoderma harzianum* with the addition of glycerol in the production medium. *Crop Protection* 30:1334-13339). Formulation studies focused on stabilization processes for *Trichoderma* biomass, aerial conidia and chlamydospores that provided adequate storage stability (Lewis J A, Papavizas G C, 1985. Characteristics of alginate pellets formulated with *Trichoderma* and *Gliocladium* and their effect on the proliferation of the fungi in soil. *Plant Pathology* 34(4): 571-577; Jin X, Custis D, 2010. Microencapsuling aerial conidia of *Trichoderma harzianum* through spray drying at elevated temperatures. *Biological Control* 56: 202-208; Yonsel Y S, Batum M S, 2010. *Trichoderma* granule production. Patent EP20080866322; Sriram et al., 2011, ibid). Despite these attempts to produce *Trichoderma* in liquid culture, low yields, long fermentation times and poor desiccation tolerance and storage stability have impaired the large-scale adoption of this production methodology by industry.

To meet the biopesticide market expectations and promote *Trichoderma*'s use as a fungicide or to promote plant health, an efficient and feasible liquid culture production technology must be developed to conceive a high quality *Trichoderma*-based product. Preferably, the *Trichoderma* would be persistence in soil and decaying plant material. To that end, many plant pathogenic fungi produce sclerotia; i.e., melanized, compact hyphal aggregates that are highly resistant to desiccation. These propagules often serve as the overwintering structure for the fungus (Cooke, 1983, Morphogenesis of sclerotia. In "Fungal Differentiation: A Contemporary Synthesis" Smith, J. E, ed. pp 397-418. Marcel Dekker, Inc., New York, N.Y., U.S.A.; Coley-Smith and Cooke, 1971, Survival and germination of fungal sclerotia. In "Annual Review of Phytopathology", Horsfall, J. G., Baker, K. F., Zentmyer, G. A., eds. pp 65-92. Annual Reviews Inc., Palo Alto, Calif., U.S.A.). Microsclerotia (small sclerotial particles, 200-600 um) of fungal plant pathogens such as *Colletotrichum truncatum* and *Mycoleptodiscus terrestris* have been produced in high concentration in submerged liquid culture fermentation (Jackson and Schisler, 1995, Mycological Research, 99:879-884; Shearer and Jackson, 2003, U.S. Pat. No. 6,569,807). Microsclerotia of these pathogens of weedy plants have shown value as persistent propagules in soil and aquatic environments (Shearer and Jackson, 2006, Biological Control. 38:298-306; Boyette et al., 2007, BioControl 52:413-426). However, to date, microsclerotia have not been reported for any *Trichoderma* species.

BRIEF SUMMARY OF THE INVENTION

Disclosed herein are isolated microsclerotia of a fungus, the composition comprising microsclerotia of a *Trichoderma* species. In one embodiment of the invention, the isolated microsclerotia are from *Trichoderma harzianum*. In another embodiment of the invention, the isolated microsclerotia are from *Trichoderma lignorum*. In yet another embodiment of the invention, the isolated microsclerotia are from *Trichoderma viridae*. In one embodiment of the invention, the isolated microsclerotia are from *Trichoderma harzianum*. In another embodiment of the invention, the isolated microsclerotia are from *Trichoderma reesei*. In yet another embodiment of the invention, the isolated microsclerotia are from *Trichoderma koningii*. In one embodiment of the invention, the isolated microsclerotia are from *Trichoderma pseudokoningii*. In yet another embodiment of the invention, the isolated microsclerotia are from *Trichoderma polysporum*. In yet another embodiment of the invention, the isolated microsclerotia are from *Trichoderma asperellum*, *Trichoderma hamatum*, *Trichoderma gamsii*, *Gliocladium virens*, and *Gliocladium catenulatum*.

Disclosed is a composition comprising microsclerotia of a fungus, the composition comprising microsclerotia of a *Trichoderma* species with an agronomically acceptable carrier which said microsclerotia, upon rehydration, germinate hyphally or sporogenically to produce conidia. In one embodiment of the invention, the microsclerotia are present in an effective amount of control a plant disease. In another embodiment of the invention, the microsclerotia are present in an effective amount to promote plant growth. In another embodiment of the invention, the microsclerotia are produced by liquid culture fermentation and are present in the recovered biomass in a concentration at least about $1 \times 10^5$ microsclerotia per gram of said biomass.

Also disclosed herein is a method for producing a fungus in a high concentration of desiccation tolerant fungal microsclerotia. The method comprise the step of inoculating a liquid culture medium comprising a carbon source and a nitrogen source with fungal propagules of a biocontrol fungus comprising a hyphae or spores of a *Trichoderma* species, said organic nitrogen source having a concentration between 8 grams/liter and 40 grams/liter and said carbon source having a concentration greater than 40 grams/liter, incubating the propagules for a sufficient time to allow for production of microsclerotia; and collecting the resulting biomass-containing microsclerotia. In one embodiment the resulting microsclerotia are storage stable after being dried. In another embodiment the resulting microsclerotia are storage stable after being applied to seeds. In another embodiment the resulting microsclerotia upon rehydration, produces conidia.

Also disclosed herein is a method for producing a fungus in a high concentration of desiccation tolerant fungal microsclerotia and submerged conidia. The method comprise the step of inoculating a liquid culture medium comprising a carbon source and a nitrogen source with fungal propagules of a fungus comprising a hyphae or spores of a *Trichoderma* species, said organic nitrogen source having a concentration between 8 grams/liter and 40 grams/liter and said carbon source having a concentration greater than 40 grams/liter, incubating the propagules in a bioreactor for a sufficient time to allow for production of microsclerotia and submerged conidia, aerating the bioreactor to an air flow that maintains dissolved oxygen levels near or above zero and providing at least 0.1 $V_{air}/V_{culture\ media}$; and collecting the resulting microsclerotia and submerged conidia. In one embodiment of the invention, about $10.8 \times 10^6$ microsclerotia per liter and about $1.9 \times 10^{12}$ submerged conidia per liter is collected from the disclosed method.

BRIEF DESCRIPTION OF THE DRAWING

The present invention together with the disclosed embodiments may best be understood from the following detailed description of the drawings, wherein:

FIGS. 2A and 2B are graphs depicting desiccation tolerance and storage stability of *Trichoderma harzianum* T-22 submerged conidia produced in various media. Dried submerged conidia were vacuum packed and stored at 4° C. Conidia germination of dried submerged conidia was assessed on water agar after 16 h incubation at 25° C. In FIG. 2A, Pair-wise comparisons between viability rates (means±SE) before and after air-drying; paired t-Student test at $P \leq 0.05$ (*), $P \leq 0.01$ (**) or not significant (ns). In FIG. 2B, full circles represent means (±SE) while lines are the fitted data by a exponential decay model: $y=40+40.3\exp(-0.72 \times time)$ ($R^2=0.75$) [30:1 C:N, 8 g $L^{-1}$], $y=7.7+71.6\exp(-0.5 \times time)$ ($R^2=0.80$) [50:1 C:N, 8 g $L^{-1}$], $y=14.1+58.7\exp(-0.39 \times time)$ ($R^2=0.79$) [30:1 C:N, 36 g $L^{-1}$], and $y=17.2+61.9\exp(-0.35 \times time)$ ($R^2=0.81$) [50:1 C:N, 36 g $L^{-1}$]. Viability decay curves were compared by the sum-of-squares reduction test and different letters indicate significant difference between curves at $P \leq 0.05$.

DETAILED DESCRIPTION OF THE INVENTION

Disclosed herein are the formation of microsclerotial propagules by *Trichoderma* and the use of those microsclerotia.

DEFINITIONS

As used in the specification and claims, the singular form "a", "an" and "the" include plural references unless the context clearly dictates otherwise. For example, the term "a cell" includes a plurality of cells, including mixtures thereof.

As used herein, the term "microsclerotia" refers to small sclerotial bodies which are some resting state of the fungi. Micro sclerotia are stable, viable, sometimes melanized, compact hyphal aggregate of the fungus. The microsclerotia per se are not infective, but when rehydrated such as by exposure to moisture in the soil or within the crevices in the bark of trees, the microsclerotia will germinate hyphally or sporogenically to produce conidia both of which are infective to the target fungal plant pathogens. The microsclerotia are extremely desiccation tolerant, are capable of germinating both sporogenically and vegetatively, and also retain the fungicidal capabilities of their native or normal forms (i.e., hyphae, blastospores, and/or conidia of the same fungus). Morphologically, the microsclerotia may be present as an agglomerated group of cells.

As used here in the term "conidia" refers to asexual, non-motile spores of a fungus. "Aerial" conidia are formed from fungal hyphae growing a solid-substrate or can form directly from sclerotial bodies including microsclerotia. Conidia formed in an aqueous environment such as liquid fermentation broth are termed "submerged" conidia.

As used herein, the term "fungicide" refers to a material or mixture of materials which induce mortality, disrupt or impede growth, and to prevent the spread of target fungi. Fungicides are also used to fight fungal infections. Fungicides can either be contact or systemic. A contact fungicide kills fungi when sprayed on its surface. A systemic fungicide has to be absorbed by the fungus before the fungus dies. The fungicidal methods disclosed herein include preventive, protective, prophylactic and eradicant treatments.

The invention described herein is effective for producing microsclerotia from any species, strain or variety of mycoparasitic fungi from the genus *Trichoderma*, although it is also envisioned that the invention may be used to produce microsclerotia from species from the genus *Gliocladium*. Preferred species for use herein include but is not limited to *Trichoderma harzianum*, *Trichoderma lignorum*, *Trichoderma viridae*, *Trichoderma reesei*, *Trichoderma koningii*, *Trichoderma pseudokoningii*, *Trichoderma polysporum*, *Trichoderma asperellum*, *Trichoderma hamatum*, and *Trichoderma gamsii*.

Production of the microsclerotia of this invention is preferably effected in liquid-culture, and large scale production is preferably conducted by deep-tank liquid-culture fermentation. It is also envisioned that solid culture media may be utilized. The liquid medium used in the preparation of the melanized microsclerotia is critical, as their formation and yield are medium dependent. For use herein, the medium preferably contains a nitrogen source at a concentration between 8 grams nitrogen source/liter and less than 40 grams nitrogen source/liter, and a carbon source at a concentration greater than 18 grams of carbohydrate/liter, preferably greater than 40 grams carbohydrate/liter. Suitable nitrogen sources include, but are not limited to hydrolyzed casein, yeast extract, hydrolyzed soy protein, hydrolyzed cottonseed protein, corn steep liquor powder, and hydrolyzed corn gluten protein. Suitable carbon sources include, but are not limited to carbohydrates, including glucose, fructose, and sucrose, and glycerol. The preferred liquid-culture media for use herein is described by Jackson (U.S. Pat. No. 5,968,808, the contents of which are incorporated by reference herein). Fungi from the genus *Trichoderma* produce microsclerotia when grown in submerged culture on the Jackson medium. These microsclerotia have not been hitherto described from these fungi. The fermentation may be conducted using conventional aerobic liquid-culture techniques with agitation and aeration. Agitation is preferred to inhibit mycelial growth on the vessel wall. Suitable temperatures may range from about 15° C. to about 32° C., and the pH may range from about 4 to about 8. Preferable temperature range for fermentation is from about 25° C. to about 30° C. Once a sufficiently heavy growth of the fungus has been obtained, usually in about 2-4 days, microsclerotia begin to form and the fermentation is then continued until a sufficiently high concentration of the microsclerotia is obtained. Without being limited thereto, in a preferred embodiment, the fermentation is continued until a major proportion of the viable fungi in the culture (i.e., greater than 30% by weight), and more preferably until a predominant proportion of the viable fungi in the culture (i.e., greater than 50% by weight) are differentiated to form microsclerotia. High sheer fermentation conditions found in some bioreactor configurations may result in microsclerotia being broken into smaller melanized, hyphal aggregates or blended formulations. These hyphal aggregates or blended formulations would propagate conidia. Following completion of the fermentation, the microsclerotia may be recovered using conventional techniques, such as by filtration or centrifugation. The microsclerotia may be dried, such as by air-drying or by application to seeds, to a low moisture level, and stored at room temperature or lower. In a preferred embodiment, the biomass recovered from the fermentation, following drying, will contain approximately $1 \times 10^5$ or higher microsclerotia per gram of biomass (based on dry weight of the biomass), particularly at least $1 \times 10^6$ microsclerotia per gram of biomass.

It is contemplated that commercial production of microsclerotia by liquid fermentation would be accomplished via fermentation in a bioreactor. Conditions in the bioreactor would form cultures of both microsclerotia and submerged conidia via liquid fermentation. It is contemplated that a person having ordinary skill in the art would be able to control the formation of microsclerotia and submerged conidia by controlling the dissolved oxygen rate in the fermentor given the teachings of media conditions disclosed herein.

Commercial formulations for use as a biocontrol against pathogenic fungi may be prepared from microsclerotia that have been harvested from the culture medium such as described herein. As a practical matter, it is envisioned that commercial formulations may be prepared directly from the culture, thereby obviating the need for any purification steps. While liquid cultures may be used directly such as in the coating of seeds, potting mix, in the preferred embodiment the water is removed from the cultures to partial or substantial dryness as described above, and the dried culture broken or ground into small particles suitable for application through conventional granule applicators, using techniques conventional in the art. To facilitate application and subsequent fungal outgrowth and conidiation, the harvested microsclerotia may alternatively be formulated in a suitable, agronomically acceptable, nutritional or inert carrier or vehicle for application as wettable powders, dusts, granules, baits, solutions, emulsifiable concentrates, emulsions, suspension concentrates and sprays (aerosols). For example, for liquid applications, the microsclerotia may be formulated as a suspension or emulsion. In this embodiment, preferred carriers include but are not limited to water, buffers, or vegetable or plant oils. In an alternative, preferred embodiment particularly suited for solid granular applications, the microsclerotia may be formulated with solid inert carriers or diluents such as diatomaceous earth, talc, clay, vermiculite, $CaCO_3$, corn cob grits, alginate gels, starch matrices or synthetic polymers, or they may be incorporated into conventional controlled release microparticles or microcapsules. The skilled practitioner will recognize that the fungi may also be formulated in combination with conventional additives such as sticking agents or adherents, emulsifying agents, surfactants, foams, humectants, or wetting agents, antioxidants, UV protectants, nutritive additives, fertilizers, or insecticides. For application onto seeds, the bark or canopy of trees, and plants, the microsclerotia are also preferably formulated with a hygroscopic or hydrophilic adjuvant. Formulations may have lower microsclerotia concentrations in which a person having ordinary skill in the art would use the microsclerotia as an agrochemical, biopesticide, pesticide, fungicide, a plant growth additive, and biostimulants.

The absolute amount of the microsclerotia and their concentration in the final composition are selected to provide an effective reduction in pathogenic fungi as compared to an untreated control. The actual amount is not critical and is a function of practical considerations such as the properties of the vehicle or carrier, the density of the target pathogenic fungi, and the method and site of application, and may be readily determined by routine testing. For a composition comprising a microsclerotium of a *Trichoderma* species with an agronomically acceptable carrier which said microsclerotia, upon rehydration, germinate hyphally or sporogenically to produce aerial conidia, for the purposes of formulation and application, an "effective amount" is defined to mean any quantity of microsclerotia sufficient to subsequently produce enough conidia in the target habitat to infect and kill the target pathogenic fungi relative to an untreated control. By way of example and without being limited thereto, it is envisioned that suitable formulations will typically contain about $1\times10^5$ or higher microsclerotia per gram of biomass recovered from the liquid culture (based on the dried weight of the biomass), preferably at least $1\times10^6$ microsclerotia per gram of biomass.

In use, the microsclerotia of this invention may be applied to the vicinity or on the surface of the plants to be protected, e.g., onto tree bark, or as a seed coating, using conventional techniques. In a preferred embodiment, the microsclerotia are applied to the soil, or to soil-less potting mixes such as are used in greenhouses, in a granular form. Depending upon the target fungal pest, the microsclerotia may be applied in agricultural fields orchards, greenhouses, gardens or lawns, or on or in the vicinity of ornamental plants, trees, or commercial or residential structures as an antagonist against plant pathogenic fungi.

In another embodiment of the invention, the microsclerotia can be applied to the vicinity or on the surface of the plants to promote plant growth and health.

The absolute amount of the microsclerotia and their concentration in the final composition are selected to provide an effective reduction in pathogenic fungi or increase plant health as compared to an untreated control. The actual amount is not critical and is a function of practical considerations such as the properties of the vehicle or carrier, the density of the target pathogenic fungi, and the method and site of application, and may be readily determined by routine testing. For the purposes of formulation and application, an "effective amount" is defined to mean any quantity of microsclerotia sufficient to subsequently produce enough hyphal growth or conidia in the target habitat to inhibit the growth and infectivity of the target pathogenic fungi relative to an untreated control. By way of example and without being limited thereto, it is envisioned that suitable formulations will typically contain about $1\times10^5$ or higher microsclerotia per gram of biomass recovered from the liquid culture (based on the dried weight of the biomass), preferably at least $1\times10^6$ microsclerotia per gram of biomass.

The microsclerotia of the *Trichoderma* species described herein produces hyphae and aerial conidia effective for control of plant pathogens. Without being limited thereto, plant pathogen which may be controlled by the microsclerotia of this invention include but are not limited to various species of *Rhizoctonia, Sclerotinia, Sclerotiorum, Fusarium, Verticillium, Phytophthora, Castenea, Armillaria, Pythium,* and *Thielviopsis.*

Statistical Analysis

Each experiment was conducted with a completely randomized design and repeated at least three times. R (R Core Team, 2012. R: *A language and environment for statistical computing.* R Foundation for Statistical Computing, Vienna, Austria) and lme4 package (Bates D M, Maechler M, Bolker B, 2012. lme4: Linear mixed-effects models using S4 classes. R package version 0.999999-0. Available at http://cran.stat.sfu.ca/web/packages/lme4/lme4.pdf) were used to perform linear mixed effects analysis for repeated measures data to address the effects of culture medium and time on biomass accumulation, submerged conidia concentration, microsclerotia concentration, conidial production from dried microsclerotia, and conidial viability. For liquid fermentation studies, treatment (i.e., culture medium), time (i.e., fermentation day or storage period) and their interaction term was entered as fixed effects into the model. As random effects, shake flask (i.e., subject or replicate) were subject to repeated observations over time and experimental repetition to account for any variation among experiments conducted at different dates. Likelihood-ratio chi-square test was employed to address the significance of fixed effects and their interaction in the linear mixed models by estimating their P-values by comparing nested models (Pinheiro J C, Bates D M, 2000. *Mixed-Effects Models in S and SPLUS.* New York: Springer. R Core Team, 2012. R: *A language and environment for statistical computing.* R Foundation for Statistical Computing, Vienna, Austria). Submerged conidia and microsclerotia production data were transformed by $\log_{10}(x+1)$ when necessary to meet the data normality and homogeneity assumptions prior to analysis. Post-hoc pairwise comparisons were carried out using the function ghlt in the multcomp package to compare treatments, correcting P-values for multiple comparisons by the single-step method. Submerged conidial viability (% germination) recorded before and after air-drying (i.e., two dependent samples) were compared by paired t-Student test to account for the impact of desiccation tolerance on submerged conidial survival within each treatment. For the longitudinal dataset on storage stability of microsclerotia, measured by conidia production over time, treatment (=culture medium) and time (months) were fitted as fixed effects, while sample packages (i.e., subjects) were considered a random effect in a linear mixed model. Then slopes for the storage stability curves were compared using a contrast matrix to assess differences among the treatments. Submerged conidia storage stability data were fitted by an exponential decay model using the function nls, and comparisons between nonlinear models were made via the sum-of-squares reduction test (Ratkowsky D, 1990. *Handbook of Nonlinear Regression Models*. New York and Basel: Marcel Dekker).

The effect of soil treatments on the proportion of melon seedlings killed by damping-off caused by *R. solani* was assessed by survival analysis (Kaplan E L, Meier P, 1958. Nonparametric estimation from incomplete observations. *Journal of the American Statistical Association* 53 (282): 457-481). Seedlings surviving beyond day 15 were considered censored. Statistically significant differences between survival curves for treatments were estimated by the log-rank test (survival package) with P-values adjusted by Bonferroni. Proportion data on total seedling emerged and healthy seedling recorded at day 15 were analyzed by a generalized linear mixed model (glmer) with treatments as fixed effect, while punnets (replicates) and bioassays (experimental repetitions) were scored as random effects.

Trichoderma Isolates

*Trichoderma harzianum* Rifai strain T-22 (ATCC 20847; Rootshield®, BioWorks, Inc., Geneva, N.Y.) was used throughout this study. Pure cultures of *T. harzianum* were isolated from serial dilutions of Rootshield® and grown on potato dextrose agar (PDA, Difco®) at 25±1° C. for at least seven days. Single colonies were purified by re-isolation on PDA and a single hyphal tip was isolated and grown on PDA. Molecular analysis of the *Trichoderma* isolate confirmed that the strain was *T. harzianum* T-22 (ATCC 20847). The sporulated colony arising from this hyphal tip was used as a stock culture of *T. harzianum* T-22 and was cut into 1 mm$^2$ pieces, placed in cryovials containing 10% glycerol, and stored at −80° C.

Other *Trichoderma* species were tested, were taken from taken from the USDA, Agricultural Research Service, Culture Collection in Peoria, Ill. Namely, *Trichoderma harzianum* (NRRL 13879), *T. harzianum* (NRRL 13019), *T. harzianum* (NRRL A-24290), *T. lignorum* (NRRL 1762), *T. viridae* (NRRL A-23264), *T. reesei* (NRRL 6156), *T. koningii* (NRRL A-18871), *T. pseudokoningii* (NRRL 22083), and *T. polysporum* (NRRL 28981). Stock cultures of each strain of *Trichoderma* spp. were grown as single spore isolates on potato dextrose agar (PDA) for three weeks at room temperatures. The sporulated plate was cut into 1 mm$^2$ agar plugs and stock cultures of these agar plugs stored in 10% glycerol at −80° C. Conidial inocula for liquid culture experiments were produced by inoculating PDA plates with a conidial suspension from the frozen stock cultures and growing these cultures at room temperature (~22° C.) for 2-3 wks. All liquid cultures were inoculated at an initial concentration of 5×10$^6$ conidia ml$^{-1}$ culture broth.

For liquid culture studies, conidial inocula were obtained by inoculating PDA plates with a conidial suspension from the frozen stock cultures and growing the cultures at 25±1° C. for 2-3 weeks. Conidial suspensions were obtained from sporulated agar plates by rinsing plates with 10 mL of a sterile solution containing 0.04% polyoxyethylene sorbitan mono-oleate (Tween 80, Sigma®)).

Growth and propagule formation by *T. harzianum* was assessed in liquid media containing different carbon concentrations, carbon-to-nitrogen (C:N) ratios, and nitrogen sources using a semi-defined liquid medium composed of basal salts with glucose (Sigma®) and acid hydrolyzed casein (Casamino Acids®, Difco Laboratories, Detroit, Mich., USA) as the carbon and nitrogen sources. The defined basal salts medium used in all liquid cultures contained per liter of double deionized water (Jackson M A, McGuire M R, Lacey L A, Wraight S P, 1997. Liquid culture production of desiccation tolerant blastospores of the bio-insecticidal fungus *Paecilomyces fumosoroseus*. *Mycological Research* 101: 35-41) KH$_2$PO$_4$, 2.0 g; CaCl$_2$.2H$_2$O, 0.4 g; MgSO$_4$.7H$_2$O, 0.3 g; FeSO$_4$.7H$_2$O, 0.05 g; CoCl$_2$.6H$_2$O, 37 mg; MnSO$_4$H$_2$O, 16 mg; ZnSO$_4$.7H$_2$O, 14 mg; thiamin, riboflavin, pantothenate, niacin, pyridoxamine, thioctic acid, 500 µg each; and folic acid, biotin, vitamin B$_{12}$, 50 µg each. The amounts of glucose and acid-hydrolyzed casein and the corresponding carbon concentrations and C:N ratios are shown in Table 1 for each culture medium tested. Carbon concentration and C:N ratio calculations were based on 40% carbon in glucose and 53% carbon, and 8% nitrogen in acid hydrolyzed casein.

All cultures were grown in 100 mL of liquid medium using 250-mL baffled, Erlenmeyer flasks (Bellco Glass, Vineland, N.J., USA) incubated at 28° C. and 300 rev.min$^{-1}$ (rpm) in a rotary shaker incubator with a 1.9 cm horizontal throw (INNOVA 4000, New Brunswick Scientific, Edison, N.J., USA). During the fermentation period, flasks were hand-shaken frequently to prevent mycelial growth on the flask wall. For C:N ratio and carbon concentration studies, media were inoculated with a conidial suspension obtained from a 2-3 weeks old sporulated agar plate of *T. harzianum* adjusted to deliver a final concentration of 5×10$^5$ conidia mL$^{-1}$ in the medium. Two, 4 and 7 days after inoculation, 3 mL samples were taken to measure biomass, submerged conidia, and microsclerotia concentrations. For each experiment, duplicate samples were taken from each flask on each sampling date, and two duplicate flasks for each treatment were used in the studies. Experiments were repeated four times.

Different Nitrogen Sources

Different nitrogen sources were evaluated for use in growing *T. harzianum* cultures based on biomass accumulation and propagule formation. The nitrogen sources were added to the basal salts medium with glucose to produce a medium with a 50:1 C:N ratio and carbon concentration of 36 g L$^{-1}$ corresponding to medium 6 from the previous experiment (see Table 1). In addition, a medium formulation containing powdered molasses (BioSev Ltd., Sao Paulo, SP, Brazil) with approximately 40% carbon was tested as a substitute for glucose as the main carbon source. The protein-based by-products tested were soyflour (Toasted Nutrisoy®, ADM Co., Decatur, Ill., USA), cottonseed flour (Pharmamedia®, ADM, Memphis, Tenn., USA), yeast extract (Difco®, Detroit, Mich., USA) and corn steep liquor powder (Solulys® AST, Roquette Corporation, Gurnee, Ill., USA). All media compositions followed by their nitrogen content are shown in Table 2. For nitrogen source evaluations, conidial inoculum of *T. harzianum* was obtained from sporulated PDA plates to provide a final concentration of 5×10$^6$ conidia mL$^{-1}$ of medium. Two agitation speeds were tested, 300 or 350 rpm, and considered a second factor in the experimental design. Samples were taken after 2 and 4 days of growth and biomass accumulation, submerged conidia and microsclerotia concentrations were measured. Each treatment was duplicated and experiments were repeated three times.

To complete the nitrogen source studies, the basal salts medium containing cottonseed flour as the nitrogen source (30:1 and 10:1 C:N ratio with carbon concentration of 36 g L$^{-1}$) was inoculated with a 3-day-old pre-culture of *T. harzianum* grown in medium 6 (Table 1). Pre-cultures were inculated with conidia using the previously described methods. Experiments were repeated three times.

TABLE 1

Media composition based on carbon concentration (g L$^{-1}$) and carbon-to-nitrogen (C:N) ratio used to assess growth, propagule formation and yields for Trichoderma harzianum T-22.

| Liquid media designation | Carbon (g L$^{-1}$) | C:N ratio | Glucose (g L$^{-1}$) | Acid hydrolyzed casein (g L$^{-1}$) |
|---|---|---|---|---|
| 1 | 8 | 10:1 | 10.0 | 10.0 |
| 2 | 8 | 30:1 | 16.6 | 3.4 |
| 3 | 8 | 50:1 | 18.0 | 2.0 |
| 4 | 36 | 10:1 | 45.0 | 45.0 |
| 5 | 36 | 30:1 | 75.0 | 15.0 |
| 6 | 36 | 50:1 | 81.0 | 9.0 |

Growth and Propagule Formation

Three mL samples were taken at various times during growth to measure biomass accumulation and conidia and microsclerotia concentrations. A wide-bore, 1-mL plastic pipette tips (tip removed with razor blade to create wider opening) were used for all sampling. For biomass accumulation measurements, one mL of the whole culture broth was taken from the flasks and the biomass was separated from the spent medium by vacuum filtration onto pre-weighed filter disks (2.4 cm glass fiber G6, Fisher Scientific, Pittsburgh, Pa., USA). Dry weight accumulation was determined by drying the biomass and filter disk at 60° C. to a constant weight prior to measurement. Submerged conidia concentrations were determined microscopically using a hemocytometer. For microsclerotia concentration measurements, 100 µL of culture broth was placed on a glass slide and overlaid with a large, 24×50 mm coverslip (Fisher Scientific, USA). All the microsclerotia on the slide were counted microscopically. Only discrete, compact hyphal aggregates larger than 50 µm in diameter were counted as microsclerotia. Culture broth was diluted as appropriate for ease in counting microsclerotia. During culture broth sampling and dilution, microsclerotia suspensions were constantly vortexed to ensure homogeneity. A hemocytometer could not be used for counting microsclerotia due to their large size. All microscopic analyses were conducted using an Olympus BH-2 microscope with Nomarski optics.

TABLE 2

Evaluation of media containing different nitrogen sources, liquid medium 6 (36 g carbon L$^{-1}$; 50:1 C:N ratio).

| Carbon Source | Protein (% Nitrogen) | Trade name | Manufacturer |
|---|---|---|---|
| Glucose | Acid hydrolyzed casein (8) | Casamino acids ® | Difco |
| Glucose | Soyflour (8.5) | Toasted Nutrisoy ® Flour | ADM, Decatur, IL, USA |
| Glucose | Cottonseed flour (9.5) | Pharmamedia ® | Traders Protein, Memphis, TN, USA |
| Glucose | Autolyzed yeast (8) | Yeast extract ® | Difco |
| Glucose | Corn steep liquor (7.2-8.2) | Solulys ® AST | Roquette Corp., Gurnee, IL, USA |
| Molasses | Acid hydrolyzed casein (8) | Casamino acids ® | Difco |

Example 1

Formulation, Desiccation Tolerance, and Storage Stability of T. harzianum

In medium evaluation studies, cultures of T. harzianum strain T-22 as described above were sampled on days 2 and 4 and harvested on day 7. At harvest on day 7, diatomaceous earth [DE (HYFLO®, Celite Corp., Lompoc, Calif., USA)] was added to the fungal biomass of each flask that contained microsclerotia and/or submerged conidia at a concentration of 5 g DE 100 mL$^{-1}$ culture broth. The culture biomass-DE mixtures were vacuum-filtered in a Buchner funnel using Whatman No. 1 filter paper. The resulting filter cake was broken up by pulsing in a blender (Mini Prep® Plus, Cuisinart, Stamford, Conn., USA), layered in Petri dish plates, and air-dried overnight at ~22° C. with a relative humidity (rh) of 50-60%. The moisture content of the microsclerotia-DE preparations was determined with a moisture analyzer (Mark II, Denver Instruments, Arvada, Colo., USA) along with their corresponding water activities, measured at an equilibrated temperature of 25° C. (AquaLab series 4TEV, Decagon Devices, Inc., Pullman, Wash., USA). When formulations of T. harzianum were dried to a moisture content of less than 4% (water activity <0.35), the dried formulations were vacuum packed in nylon polyethylene bags (15.3×21.8 cm) with a vacuum packer (Multivac C 100, Sepp Haggenmüller, Wolfertschwen-den, Germany) and stored at 4° C.

To compare storage stability of Trichoderma microsclerotia under room and refrigerated temperatures, a hundred mL cultures of T. harzianum T-22 were grown in medium 10:1 and 30:1 C:N ratio with cottonseed flour as the nitrogen source, harvested on day 4, formulated with 5% DE (w/v), and air-dried to less than 4% moisture. Air dried microsclerotia formulations were vacuum packed in 15×22 cm aluminized Mylar bags (PAKVF4, IMPAK Corporation, Los Angeles, Calif., USA) and kept in ambient (25° C.) or refrigerated (4° C.) conditions.

For testing microsclerotia viability and submerged conidia production, methodology was adapted from Jackson M A, Jaronski S T, 2009. Production of microsclerotia of the fungal entomopathogen *Metarhizium anisopliae* and their potential for use as a biocontrol agent for soil-inhabiting insects. *Mycological Research* 113: 842-850. Briefly, 25 mg of dried microsclerotia-DE preparations of T. harzianum were inoculated on water agar (2% w/v) plates and incubated at 25° C. Upon rehydration, the microsclerotia granules germinated myceliogenically (germ tube formation) and sporogenically (production of conidia). Two water agar plates (subsamples) were used for each treatment replicate. Following a 24 h incubation at 25° C., one hundred microsclerotia-DE granules per plate were examined with a stereo microscope (Olympus, model SZH10) for hyphal germination as a measure of viability. To enumerate conidia production, water agar plates were kept at 25° C. for a total of seven days. Each plate then was flooded with 7 mL of 0.04% Tween 80 solution and the conidia were dislodged from the microsclerotia-DE granules using a sterile loop. After the conidia were dislodged, the available liquid was pipetted from each plate, and the liquid volume measured. The concentration of conidia in the pipetted liquid was measured microscopically using a hemocytometer and the total number of conidia per plate calculated. To determine the number of conidia of T. harzianum produced per gram of air-dried microsclerotia-DE preparation, the number of conidia harvested per plate was divided by the weight of the dried microsclerotia-DE preparation added to each water agar plate (0.025 g).

For submerged conidia viability assays, 0.01 g of each dried submerged conidia-DE formulation was diluted in 10 mL of 0.04% Tween 80 (Sigma®), vortexed for 1 min, and DE particles allowed to settle for 1 min. Two aliquots of 100 µL of the supernant containing mainly submerged conidia were inoculated on water agar (1% agar w/v) plates to deliver approximately 1×10⁵ submerged conidia per plate. Preliminary studies revealed no significant differences between PDA and water agar for germination assessment. Germination was assessed microscopically by evaluating 200 submerged conidia per water agar plate using an inverted microscope (Olympus IMT-2) after 16 h incubation at 25° C. Submerged conidia were considered germinated when the germ tube was larger than the diameter of the conidium. Desiccation tolerance was expressed as percentage submerged conidia survival and each treatment replicate had two subsamples. Further evaluations were conducted monthly until spore viability was less than 40%.

Under shake-flask culture conditions, the formation of submerged conidia and microsclerotia of *T. harzianum* T-22 was observed and monitored over a 7-day-fermentation period in liquid culture media with different C:N ratios. Microsclerotia of *T. harzianum* were exclusively formed and developed in high carbon media (36 g L$^{-1}$), regardless of the C:N ratio tested. The richest medium (#4) with a 10:1 C:N ratio lacked the production of submerged conidia, but promoted the development of microsclerotia. Fully formed microsclerotia of *T. harzianum* were 90-600 μm in diameter. According to the linear mixed effects model accounting for repeated measures over time, microsclerotia production by *T. harzianum* was affected by both culture medium ($\chi^2_{(15)}$=264.84, P<0.0001) and fermentation time ($\chi^2_{(12)}$=32.09, P=0.0013). The interaction between fermentation time and culture medium contributed greatly for the variation in production rates of microsclerotia ($\chi^2_{(12)}$=20.78, P=0.023) (Table 3). In general, more microsclerotia were produced by day 4 in all culture media (2.6-4.8×10⁴ mL$^{-1}$), with fewer microsclerotia observed on day 7, likely due to microsclerotia aggregation. Microsclerotia of *T. harzianum* began to form after 48 h growth with microsclerotia becoming more well-defined and compact by day 4 and melanization by day 7. While microsclerotia were more compact and melanized, these structures presented short hyphal extensions emanating from their surface. microsclerotia concentrations were seen by day 4 in media 4 and 5 while higher numbers of immature microsclerotia were present in medium 6 by day 2.

Submerged conidiation was supported by all media tested except medium 4 that produced only microsclerotia. These submerged conidia were formed by conidiogenous cells (e.g., phialides) attached to submerged hyphae in early stages (day 2) of growth especially when the fungus was grown in the weak medium (8 g carbon L$^{-1}$). After 4 days growth, submerged conidia were produced in high concentrations in those cultures with high carbon levels and lower nitrogen concentrations (50:1, 30:1 C:N ratios; Table 3). Production rates for submerged conidia were significantly affected by the interaction of culture medium×fermentation time ($\chi^2_{(15)}$=904.97, P<0.0001). A significant overall increase in submerged conidia production over time was noted in all culture media ($\chi^2_{(12)}$=980.8, P<0.0001), with higher numbers of submerged conidia achieved by day 7. Medium 1, 2 and 3 which contained lower carbon concentrations reached maximum submerged conidial production by day 4 (1.6-3.2×10⁸ conidia mL$^{-1}$), while rich-carbon media 5 and 6 attained maximum production by day 7 (3.9-9.7×10⁸ conidia mL$^{-1}$). The higher submerged conidia concentrations observed in carbon-rich media were expected as the higher availability of nutrients in these media promoted better vegetative growth and subsequent conidiation ($\chi^2_{(15)}$=1028.2, P<0.0001). Cultures of *T. harzianum* grown in carbon-limited media (media 1, 2, and 3) produced high amounts of submerged conidia within 2 days (6.5-7.7×10⁷ conidia mL$^{-1}$), whereas medium 6 (C:N ratio 50:1 and 36 g carbon L$^{-1}$) produced significantly more submerged conidia (9.7×10⁸ conidia mL$^{-1}$ by day 7.

TABLE 3

Evaluation of submerged conidia, microsclerotia (MS), and biomass production by cultures of *Trichoderma harzianum* T-22 grown in media with different C:N ratios and carbon concentrations at 28° C. and 300 rpm in a rotary shaker incubator.

| Medium | Carbon (g L$^{-1}$) | C:N ratio | Submerged Conidia (×10⁷ conidia mL$^{-1}$) | | | Microsclerotia (×10³ MS mL$^{-1}$) | | |
|---|---|---|---|---|---|---|---|---|
| | | | Day 2 | Day 4 | Day 7 | Day 2 | Day 4 | Day 7 |
| 1 | 8 | 10:1 | 6.5 a† | 25.4 ab | 27.1 bc | 0 b | 0 b | 0 b |
| 2 | 8 | 30:1 | 7.7 a | 32.1 a | 33.6 b | 0 b | 0 b | 0 b |
| 3 | 8 | 50:1 | 3.4 b | 15.8 b | 20.5 c | 0 b | 0 b | 0 b |
| 4 | 36 | 10:1 | 0 c | 0 c | 0 d | 27.8 a | 48.3 a | 15.3 a |
| 5 | 36 | 30:1 | 0 c | 0 c | 39.1 b | 22.2 a | 33.3 a | 16.6 a |
| 6 | 36 | 50:1 | 0 c | 49.9 a | 95.5 a | 32.8 a | 25.8 a | 25.9 a |

| Medium | Carbon (g L$^{-1}$) | C:N ratio | Biomass (mg mL$^{-1}$) | | |
|---|---|---|---|---|---|
| | | | Day 2 | Day 4 | Day 7 |
| 1 | 8 | 10:1 | 7.7 c | 5.6 c | 4.9 d |
| 2 | 8 | 30:1 | 5.0 d | 7.1 c | 8.5 c |
| 3 | 8 | 50:1 | 3.5 d | 4.7 d | 4.5 d |
| 4 | 36 | 10:1 | 10.0 b | 16.1 a | 19.3 a |
| 5 | 36 | 30:1 | 12.4 a | 16.3 a | 16.8 b |
| 6 | 36 | 50:1 | 10.4 b | 13.4 b | 16.3 b |

†Means followed by different letters within a column are significantly different (P ≤ 0.05).

Biomass accumulation (mg mL$^{-1}$) followed the predicted pattern in that fungal growth in carbon-limited media (8 g L$^{-1}$) resulted in less biomass when compared to cultures grown in media with 36 g L$^{-1}$ carbon, regardless of the C:N ratio (Table 3). This difference was significant by the interaction of culture medium and fermentation time ($\chi^2_{(10)}$=122.95, P<0.0001). Media 4, 5 and 6 which contained higher carbon concentrations induced increased biomass accumulation over time ($\chi^2_{(12)}$=185.4, P<0.0001). As expected, medium 4 produced the most biomass at all evaluation days, having the highest concentrations of carbon and nitrogen (C:N=10:1 and 36 g L$^{-1}$ carbon) ($\chi^2_{(15)}$=247.14, P<0.0001). Fungal biomass decreased linearly with fermentation days for medium 1, the medium poorest in carbon and nitrogen. Microscopic examination revealed that hyphal growth increased over time in carbon-rich media followed by the rapid formation of microsclerotia.

Desiccation Tolerance and Storage Stability of *T. harzianum* T-22 Propagules

Figure 1:
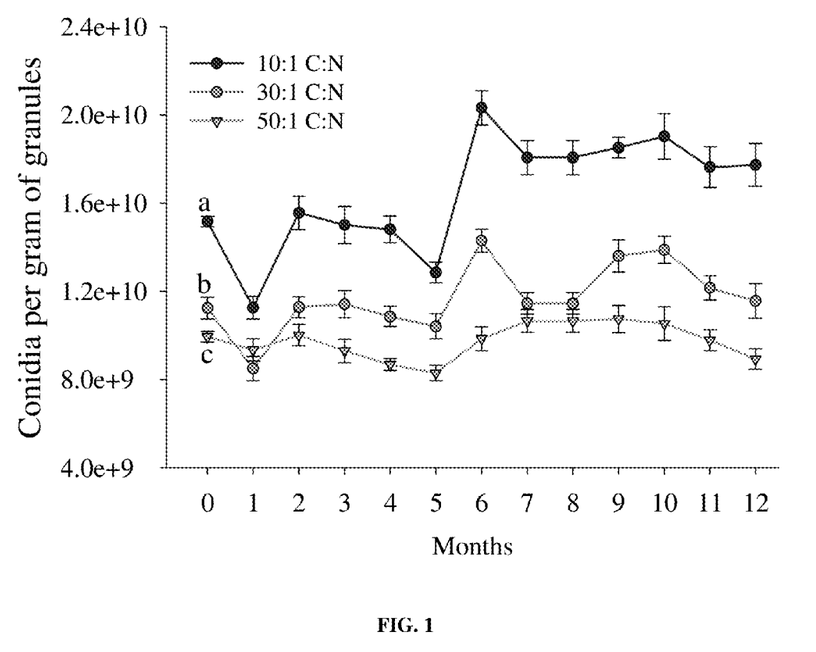
FIG. 1 is a graph depicting the impact of C:N ratio (36 g carbon $L^{-1}$) on conidia production by dried microsclerotial (MS) granules of *Trichoderma harzianum* T-22 formulated with 5% diatomaceous earth after air-drying and during long-term storage under refrigerated conditions (4° C.). Conidia production were assessed after MS granules were incubated on water agar for 7 days at 25° C. Means (±SE) at time "0" referred to desiccation tolerance and different letters indicate significantly differences ($P \leq 0.05$).

*T. harzianum* T-22 were prepared as disclosed above. After 7 days growth, all *T. harzianum* cultures from the C:N ratio studies were air dried to 0.8 to 3.8% moisture with corresponding water activity (Aw) measurements in a range of 0.35-0.41, and vacuum-packaged for storage at 4° C. Upon rehydration and incubation for 24 h, 100% of the dried microsclerotia granules germinated hyphally and aerial conidia were starting to be produced on hyphal extensions and on the surface of microsclerotia granules as noted by their light greenish coloration. These microsclerotia granules continued to germinate sporogenically producing conidia with culture medium influencing conidia production for air-dried microsclerotia granules ($\chi^2_{(2)}$=31.08, P<0.0001). Microsclerotial granules derived from media with a 10:1 CN ratio yielded 35% and 52% more conidia compared with microsclerotia granules harvested from 30:1 and 50:1 C:N ratio media, respectively (FIG. 1). For dried microsclerotia granules stored at 4° C., the production of conidia was significantly affected by both culture medium ($\chi^2_{(4)}$=98.4, P<0.0001) and storage period ($\chi^2_{(3)}$=47.2, P<0.0001). As the interaction of these two factors was also significant ($\chi^2_{(2)}$=13.23, P=0.0013), the slopes for the storage stability curves are statistically different which indicates a considerable variation in conidia production over storage time across the culture media tested. The 12-month storage stability pattern (FIG. 1) measured as conidia production from rehydrated microsclerotia granules differed only between medium 4 (10:1 C:N ratio) and medium 6 (50:1 C:N ratio) (P=0.0007), whereas no difference in temporal conidia production was found among medium 5 (30:1 C:N ratio) and the others (P>0.05). Conidia production by microsclerotia granules harvested from media with a 10:1 C:N ratio and 36 g carbon L$^{-1}$ (medium 4) remained high (1.13–2.03×10$^{10}$ conidia g$^{-1}$) over 12 months storage with a significant increase in conidia production after 6 months storage. Microsclerotial granules from the 30:1 C:N ratio medium exhibited the second highest conidia production while those produced in medium 6 (50:1 C:N ratio) attained the lowest yield. Regardless the differences in conidia production by microsclerotia granules from different culture media, conidia production for each treatment was not reduced over time which indicates these microsclerotia granules remained stable under cool storage for up to 12 months.

Figure 2:
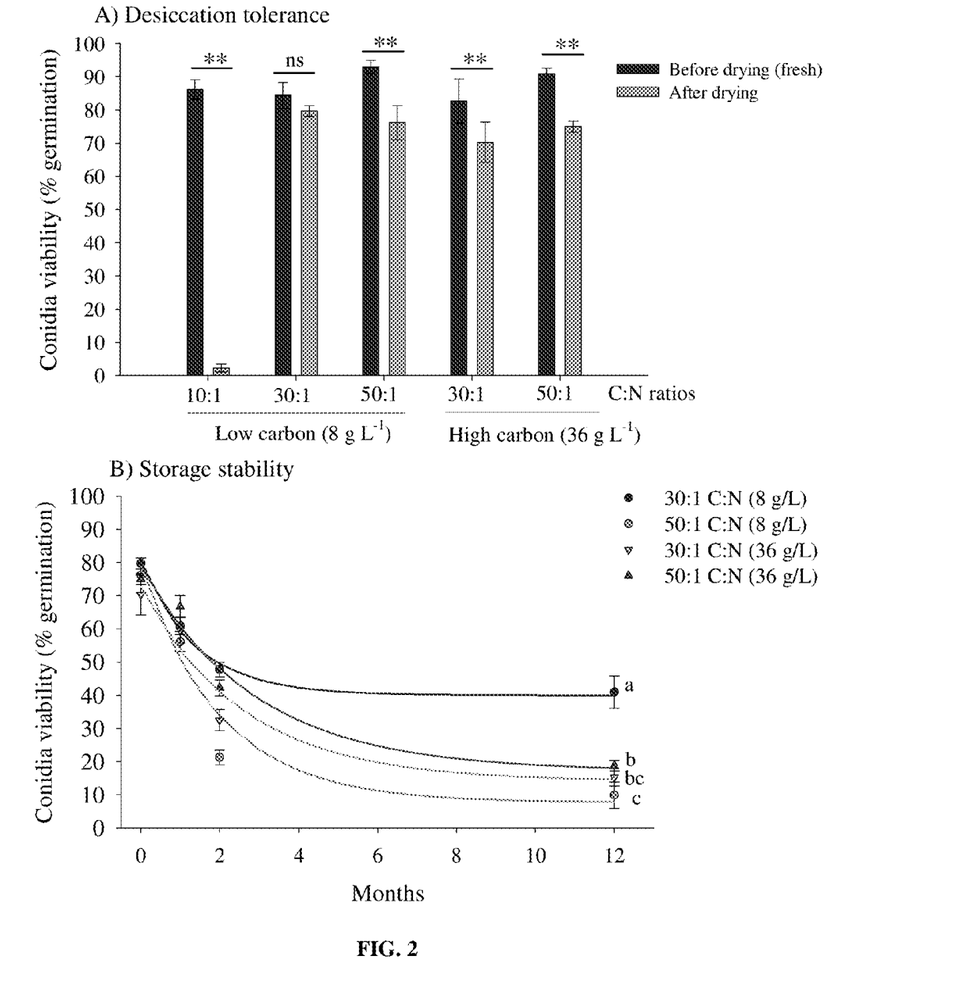

The viability and stability of submerged conidia produced in different culture media and harvested after 7 days growth were assessed before and after drying and then 1, 2 and 12 months after storage at 4° C. Only submerged conidia produced in medium 2 (8 g carbon L$^{-1}$, 30:1 C:N ratio) did not suffer a significant reduction in germination after drying when compared to fresh submerged conidia (paired $t_{(5)}$=1.23, P=0.273), whereas submerged conidia from the other media tested exhibited a significantly lower desiccation tolerance (paired t-test: P<0.01) (FIG. 2). Fresh submerged conidia from medium 1 (limited-nutrient) had the highest germination rate (84.3% viability) for fresh submerged conidia but the poorest desiccation tolerance (2.1% viability) (FIG. 2). A nonlinear exponential decay model was used to explain the relationship between storage time and submerged conidial viability in each treatment with a confidence of $R^2$=0.75-0.81. According to the models fitted to our experimental viability data recorded over time, half-lives of stored submerged conidia were estimated in 1.93, 1.05, 1.26, and 1.81 month when harvested from media 2, 3, 5, and 6, respectively. Medium 2 (low carbon and 30:1 C:N ratio) and 6 (high carbon, low nitrogen 50:1 C:N ratio) exhibited the highest germination rates by month 2, although viability decreased significantly after 12 months storage with submerged conidia from medium 3 (low carbon and 50:1 C:N ratio) being the most viable (41% survival). A comparison of survival curves showed that submerged conidia harvested from medium 3 survived longer in storage when compared to those submerged conidia produced in the other media (P<0.01).

Example 2

Effect of Agitation Speed and Nitrogen Sources on *T. harzianum* T-22 Liquid Fermentation Fermentation studies with different nitrogen sources at nutrient concentrations conducive to microsclerotia formation revealed that microsclerotia formation occurred to varying degrees with all nitrogen sources tested (Table 4). Substitution of molasses for glucose as the carbon source inhibited microsclerotia formation. All carbon and nitrogen sources tested at 50:1 (C:N ratio) with 36 g carbon L$^{-1}$ resulted in the production of both submerged conidia and microsclerotia, with the exception of the molasses treatment that only produced submerged conidia. Increasing the agitation speed from 300 to 350 rpm did not affect the production of submerged conidia ($\chi^2_{(1)}$=3.11, P=0.08), microsclerotia yields ($\chi^2_{(1)}$=1.06, P=0.302), or biomass accumulation ($\chi^2_{(1)}$=2.16, P=0.142). Thus, the experimental data obtained during growth at 300 and 350 rpm were grouped together for analysis. Based on microsclerotia yields, cottonseed flour combined with glucose at 36 g carbon L$^{-1}$ and 50:1 C:N ratio produced significantly higher numbers of microsclerotia from day 2 to 4 compared with the other nitrogen compounds tested ($\chi^2_{(10)}$=137.56, P<0.0001, Table 4). Overall, microsclerotia formation increased over fermentation time, regardless of the nitrogen source employed ($\chi^2_{(6)}$=34.14, P<0.0001). Interaction of culture medium×days of fermentation had a significant impact on microsclerotia production ($\chi^2_{(5)}$=13.17, P=0.022), indicating that growth rates for microsclerotia differed according to culture media.

TABLE 4

Evaluation of submerged conidia, microsclerotia (MS), and biomass production by cultures of *Trichoderma harzianum* T-22 grown in a liquid culture medium with different nitrogen sources, a C:N ratio of 50:1, and carbon concentration of 36 g L$^{-1}$. Cultures were incubated at 28° C. and either 300 or 350 rpm in a rotary shaker incubator.

| Carbon source | Nitrogen source | Submerged Conidia (×10$^7$ conidia mL$^{-1}$) | | Microsclerotia (×10$^3$ MS mL$^{-1}$) | |
|---|---|---|---|---|---|
| | | Day 2 | Day 4 | Day 2 | Day 4 |
| Glucose | Acid hydrolyzed casein | 33.3 a† | 80.5 a | 25.4 ab | 31.9 ab |
| Glucose | Soyflour | 4.6 b | 13.5 b | 8.8 b | 19.9 b |
| Glucose | Cottonseed flour | 2.1 b | 4.5 c | 66.0 a | 115.4 a |

TABLE 4-continued

Evaluation of submerged conidia, microsclerotia (MS), and biomass production by cultures of Trichoderma harzianum T-22 grown in a liquid culture medium with different nitrogen sources, a C:N ratio of 50:1, and carbon concentration of 36 g L$^{-1}$. Cultures were incubated at 28° C. and either 300 or 350 rpm in a rotary shaker incubator.

| Glucose | Yeast extract | 0 d | 24.5 b | 10.5 b | 20.8 b |
| Glucose | Corn steep liquor | 0 d | 14.6 b | 0.21 c | 0.41 c |
| Molasses | Acid hydrolyzed casein | 19.4 a | 24.4 b | 0 d | 0 d |

| Carbon source | Nitrogen source | Biomass (mg mL$^{-1}$) | |
| --- | --- | --- | --- |
| | | Day 2 | Day 4 |
| Glucose | Acid hydrolyzed casein | 11.2 c | 15.3 b |
| Glucose | Soyflour | 15.5 b | 19.8 a |
| Glucose | Cottonseed flour | 15.5 b | 19.9 a |
| Glucose | Yeast extract | 12.4 c | 15.1 b |
| Glucose | Corn steep liquor | 11.2 c | 14.6 b |
| Molasses | Acid hydrolyzed casein | 19.5 a | 21.8 a |

†Means followed by different letters within a column are significantly different (P ≤ 0.05). Data were combined from experiments performed with different agitation speeds, as there was no significant difference between 300 and 350 rpm.

Media composition had a significant affect on the formation and melanization of *T. harzianum* microsclerotia particularly when different nitrogen sources were used. For example, microsclerotia produced with cottonseed flour (Pharmamedia®) were highly melanized as indicated by their darker coloration; whereas those microsclerotia produced with acid hydrolyzed casein were lighter color and less compact after 4 days growth. Furthermore, microsclerotia were formed by day 4 as these propagules became more distinct, melanized and compact, especially when grown with cottonseed flour. No microsclerotia formed in medium amended with molasses+acid hydrolyzed casein, and microsclerotia numbers were reduced in media containing glucose+corn steep liquor (≤400 microsclerotia mL$^{-1}$).

For submerged conidia, production was significantly influenced by the interaction between media composition and fermentation time ($\chi^2_{(5)}$=406.3, P<0.0001). Submerged conidia production increased over time in all media tested ($\chi^2_{(6)}$=453.21, P<0.0001) other than the molasses+acid hydrolyzed casein medium. Cultures grown in media with glucose+cottonseed flour produced the highest submerged conidial yields in 4 days of fermentation ($\chi^2_{(10)}$=472.6, P<0.0001). The media composition and fermentation time acted independently and did not have an effect on biomass accumulation ($\chi^2_{(5)}$=7.92, P=0.161). Cultures grown in media containing molasses+acid hydrolyzed casein produced more fungal biomass ($\chi^2_{(10)}$=98.24, P<0.0001), than cultures grown in media amended with glucose+yeast extract, glucose+acid hydrolyzed casein or glucose+corn steep liquor (Table 4).

Figure 3:
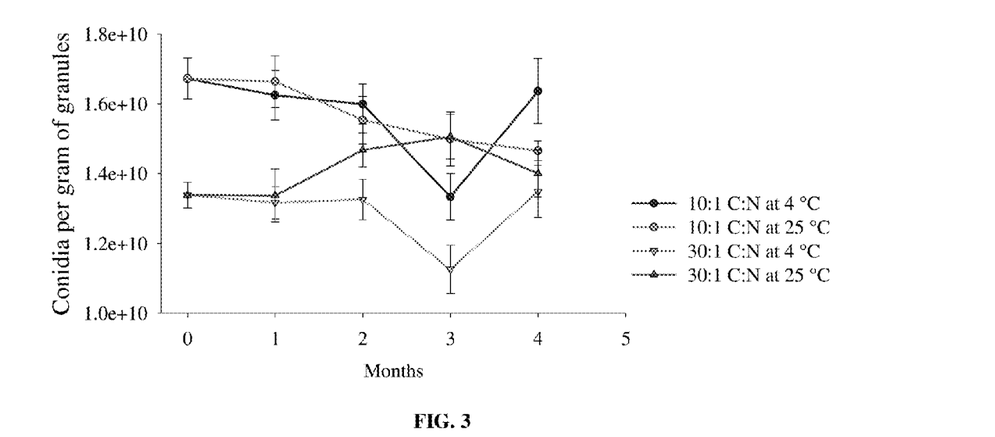
FIG. 3 is a graph depicting storage stability of microsclerotial (MS) granules of *Trichoderma harzianum* T-22 produced in various liquid media using cottonseed flour as the nitrogen source. Cultures were harvested after 4 days growth at 28° C. and 350 rpm in a rotary shaker incubator. Micro sclerotia-containing cultures were mixed with diatomaceous earth, dewatered, and air dried to less than 4% moisture and stored vacuum packed at 4° C. or 25° C.

Using cottonseed flour as the nitrogen source and a pre-culture inoculum, microsclerotia production was significantly affected by both C:N ratio ($\chi^2_{(2)}$=6.5, P=0.039) and fermentation time ($\chi^2_{(2)}$=16.51, P=0.0003), but not by their interaction ($\chi^2_{(1)}$=2.05, P=0.152) indicating that growth rates were similar. More microsclerotia were produced by day 2 in cultures grown in media with a 10:1 C:N ratio compared to media with a 30:1 C:N ratio, whereas by day 3, microsclerotia concentrations were lower in both media with no statistical difference (Table 5). *Trichoderma harzianum* grew faster producing more biomass in media with more nitrogen and a 10:1 C:N ratio. There was a significant effect of both C:N ratio ($\chi^2_{(2)}$=66.25, P<0.0001) and fermentation time ($\chi^2_{(2)}$=26.34, P<0.0001) and their interaction ($\chi^2_{(2)}$=10.8, P=0.001) on biomass accumulation, which indicates that biomass development between media assumed different rates. In agreement with these data, dried microsclerotia granules from cultures grown in 10:1 C:N ratio media produced 25% more conidia compared with microsclerotia granules from cultures grown in the 30:1 C:N ratio medium ($\chi^2_{(1)}$=17.95, P<0.0001) when rehydrated and incubated on water agar. Nonetheless, microsclerotia granules of both media were desiccation tolerant showing 100% hyphal germination after 24 h incubation. The storage stability study revealed that conidia production by microsclerotia granules was generally higher in medium with higher nitrogen content (10:1 C:N ratio) ($\chi^2_{(10)}$=47.14, P<0.0001) and variable across temperature ($\chi^2_{(10)}$=32.93, P=0.0003) and storage month ($\chi^2_{(16)}$=46.63, P<0.0001) (FIG. 3). There was a general decline in conidia production over time for microsclerotia granules from 10:1 C:N ratio stored at 25° C., whereas conidia production increased for microsclerotia from 30:1 C:N ratio medium stored at this same temperature ($\chi^2_{(8)}$=25.16, P=0.0015).

TABLE 5

Evaluation of C:N ratio on microsclerotia (MS) and biomass production by cultures of Trichoderma harzianum T-22 grown in liquid media with 36 g carbon L$^{-1}$ and cottonseed flour as the nitrogen source.

| C:N Ratio | Microsclerotia (×10$^3$ MS mL$^{-1}$) | | Biomass (mg mL$^{-1}$) | | Aerial Conidia Production (g$^{-1}$ dried MS granule)$^a$ |
| --- | --- | --- | --- | --- | --- |
| | Day 2 | Day 4 | Day 2 | Day 4 | |
| 10:1 | 5.9 a | 3.6 a | 27.8 a | 28.6 a | 1.7 × 10$^{10}$ a |
| 30:1 | 4.4 b | 3.3 a | 16.3 b | 19.0 b | 1.3 × 10$^{10}$ b |

$^a$Conidia production on water agar by rehydrated MS granules after 7 days incubation at 25° C.
†Means within a column that are not followed by the same letter are significantly different (P ≤ 0.05).

Example 3

Liquid Culture Production of Microsclerotia of a Plurality of *Trichoderma* spp.

A plurality of *Trichoderma* spp. were tested in liquid culture production of microsclerotia and biomass under shake flask conditions as described in Example 1. These *Trichoderma* cultures were grown in liquid culture medium 6 (Table 1) using cottonseed flour rather than acid hydrolyzed casein as the nitrogen source. As disclosed in Table 6, a plurality of *Trichoderma* species were able to form microsclerotia under the stated conditions. After 7 days growth, the microsclerotia were harvested from the culture broth by adding diatomaceous earth (DE) at 5% w/v and filtering under vacuum to remove the spent culture medium. The DE-microsclerotia filter cake was crumbled in a blender and air dried overnight to less than 5% moisture.

TABLE 6

Liquid culture production of microsclerotia by various species of *Trichoderma* using a basal salts medium supplemented with glucose and cottonseed flour. Cultures grown for 7 days at 350 rpm and 28° C. in a rotary shaker incubator

| Genus Species | Culture Accession Number * | Microsclerotia ($L^{-1}$) | Biomass (g $L^{-1}$) |
|---|---|---|---|
| *Trichoderma harzianum* | NRRL 13879 | $2.0 \times 10^6$ | 29.4 |
| *T. harzianum* | NRRL 13019 | $2.0 \times 10^7$ | 21.5 |
| *T. harzianum* | NRRL 54962 | $1.9 \times 10^6$ | 22.4 |
| *T. harzianum* | ATCC 20847 (T-22) | $1.2 \times 10^7$ | 19.9 |
| *T. lignorum* | NRRL 1762 | $5.3 \times 10^6$ | 25.9 |
| *T. viridae* | NRRL 66084 | $1.1 \times 10^6$ | 18.8 |
| *T. reesei* | NRRL 6156 | $9.7 \times 10^5$ | 25.9 |
| *T. koningii* | NRRL 66085 | $1.0 \times 10^6$ | 26.8 |
| *T. pseudokoningii* | NRRL 22083 | $1.0 \times 10^6$ | 14.2 |
| *T. polysporum* | NRRL 28981 | $2.4 \times 10^6$ | 14.4 |
| *T. hamatum* | NRRL 22973 | $8.6 \times 10^6$ | 32.1 |
| *T. asperellum* | ATCC 204424 | $1.0 \times 10^6$ | 30.6 |

* NRRL Culture Collection—USDA, Agricultural Research Service, National Center for Agricultural Utilization Research, Peoria, IL, 61604.
ATCC—American Type Culture Collection, Manassas, VA, 20110

Example 4

Conidia Production by Dried Microsclerotial Granules

For determining conidia production by air dried microsclerotial granules of various *Trichoderma* species, methods were adopted from Jackson M A, Jaronski S T, 2009. Production of microsclerotia of the fungal entomopathogen *Metarhizium anisopliae* and their potential for use as a biocontrol agent for soil-inhabiting insects. *Mycological Research* 113: 842-850. Briefly, 25 mg of dried microsclerotia-DE preparations of *Trichoderma* were inoculated on water agar (2% w/v) plates and incubated at 25° C. Upon rehydration, the microsclerotia granules germinated myceliogenically (germ tube formation) and sporogenically (production of conidia). Two water agar plates (subsamples) were used for each treatment replicate. Following a 24 h incubation at 25° C., one hundred microsclerotia-DE granules per plate were examined with a stereo microscope (Olympus, model SZH10) for hyphal germination as a measure of viability. To enumerate conidia production, water agar plates were kept at 25° C. for a total of seven days. Each plate then was flooded with 7 mL of 0.04% Tween 80 solution and the conidia were dislodged from the microsclerotia-DE granules using a sterile loop. After the conidia were dislodged, the available liquid was pipetted from each plate, and the liquid volume measured. The concentration of conidia in the pipetted liquid was measured microscopically using a hemocytometer and the total number of conidia per plate calculated. To determine the number of conidia of *Trichoderma* produced per gram of air-dried microsclerotia-DE preparation, the number of conidia harvested per plate was divided by the weight of the dried microsclerotia-DE preparation added to each water agar plate (0.025 g).

TABLE 7

Conidia production by dried microsclerotial (MS) granules of various *Trichoderma* species formulated with 5% diatomaceous earth after air-drying. Conidia production was assessed after MS granules were incubated on water agar for 7 days at 25° C.

| Genus Species | Culture Accession Number * | Conidia Production ($g^{-1}$ Dry formulation) |
|---|---|---|
| *Trichoderma harzianum* | NRRL 13879 | $1.5 \times 10^{10}$ +/− 0.07 |
| *T. harzianum* | NRRL 13019 | $1.5 \times 10^{10}$ +/− 0.14 |
| *T. harzianum* | NRRL 54962 | $1.1 \times 10^{10}$ +/− 0.05 |
| *T. harzianum* | ATCC 20847 (T-22) | $9.2 \times 10^9$ +/− 0.14 |
| *T. lignorum* | NRRL 1762 | $2.2 \times 10^{10}$ +/− 0.14 |
| *T. viridae* | NRRL 66084 | $3.0 \times 10^{10}$ +/− 0.14 |
| *T. reesei* | NRRL 6156 | $2.5 \times 10^9$ +/− 0.19 |
| *T. koningii* | NRRL 66085 | $6.5 \times 10^9$ +/− 0.44 |
| *T. pseudokoningii* | NRRL 22083 | $4.6 \times 10^9$ +/− 0.96 |
| *T. polysporum* | NRRL 28981 | $1.1 \times 10^9$ +/− 0.68 |
| *T. hamatum* | NRRL 22973 | $3.9 \times 10^9$ +/− 1.01 |
| *T. asperellum* | ATCC 204424 | $6.5 \times 10^9$ +/− 1.68 |

* NRRL—Culture Collection, USDA, Agricultural Research Service, National Center for Agricultural Utilization Research, Peoria, IL, 61604
ATCC—American Type Culture Collection, Manassas, VA, 20110

Example 5

Bioassay of Microsclerotia Effect on Damping-Off Disease

Bioassays with Cantaloupe melon (cv. 'Hales Best') were conducted to assess the bioefficacy of *T. harzianum* (T-22) microsclerotia produced in liquid culture (36 g C; 30:1 C:N ratio; harvested on day 4 and formulated with 5% diatomaceous earth [Hyflo®]). The damping-off pathogen, *Rhizoctonia solani* NRRL 22805 (Agricultural Research Service (NRRL) Culture Collection) was grown in Petri plates of CV8 agar for three days at 25° C. In a 100 mL Erlenmeyer flask, 25 $cm^3$ (~8.5 g) of washed and dried pulverized rice hulls (~1 $mm^3$ particles) were combined with 6 mL of 10% tryptic soy broth (Difco Laboratories, Detroit, Mich.) and 12 mL of double-deionized water. Flasks were autoclaved for 30 minutes on three consecutive days. The sterile rice hulls were then inoculated with ten, 1 $mm^2$ colonized-agar plugs of *R. solani*, incubated at 25° C., and shaken daily for eight days to assure homogenous colonization of individual particles. One day prior to experimentation, a small sample of the infested rice hulls was plated on CV8 medium to assure culture purity. Bioassay experiment treatments consisted of *R. solani* alone (1.5 and 0.625 g of infested rice hulls/1000 $cm^3$ of non-steamed Terra-lite RediEarth® potting mix (W. R. Grace, Cambridge, Mass.), *R. solani* (both inoculum doses)+*T. harzianum* (0.4 g air-dried microsclerotia/1000 $cm^3$ of potting mix), *T. harzianum* only and a non-inoculated control. These treatments were homogenized in plastic bags and shaken vigorously prior to sowing. The experiments were conducted in punnets (18×13×5.5 cm) containing six cells, and each treatment had two replications (punnets). In each cell (5.5×5×5.5 cm), a small square of paper (Wypall®, Kimberly-Clark Professional, USA) was placed on the bottom to prevent potting mix from leaking out of punnets. One quarter of a cup (59.15 $cm^3$) of non-sterile, uninoculated potting medium was added to the bottom of each cell. Forty-four $cm^3$ of the single or mixed treatments (infested with *R. solani* and/or treated with *T. harzianum*) were then layered on top of the uninoculated potting mix. Three melon seeds then were sown within the treatment mix layer at a depth of 0.5 cm and then placed in a growth chamber at 26° C. and 14 h photophase. Punnets were top-watered the first two days after sowing and then kept in separate plastic trays with adequate water to maintain potting mix wetness. Evaluations were made daily to enumerate the proportion of emerged seedlings and dead seedlings showing symptoms of damping-off caused by R. solani until day 15 after sowing. The experiment was repeated three times on different days with time considered a block effect. From those seedlings showing symptoms of damping-off, samples from the necrotic tissue immediately above the root system (i.e., hypocotyl stem) were cut and surface sterilized with a sodium hypochlorite solution (0.35% v/v) and rinsed three times with sterile double-deionized water. Samples were then plated on Martin's rose-bengal (MRB) agar (Martin, 1950) to confirm the association of R. solani with damped off seedlings. To ascertain if T. harzianum was able to colonize the root system of melon, samples of roots from seedlings grown in potting mix treated only with this fungus were surface sterilized, as previously mentioned, and then plated on MRB agar.

Figure 4:
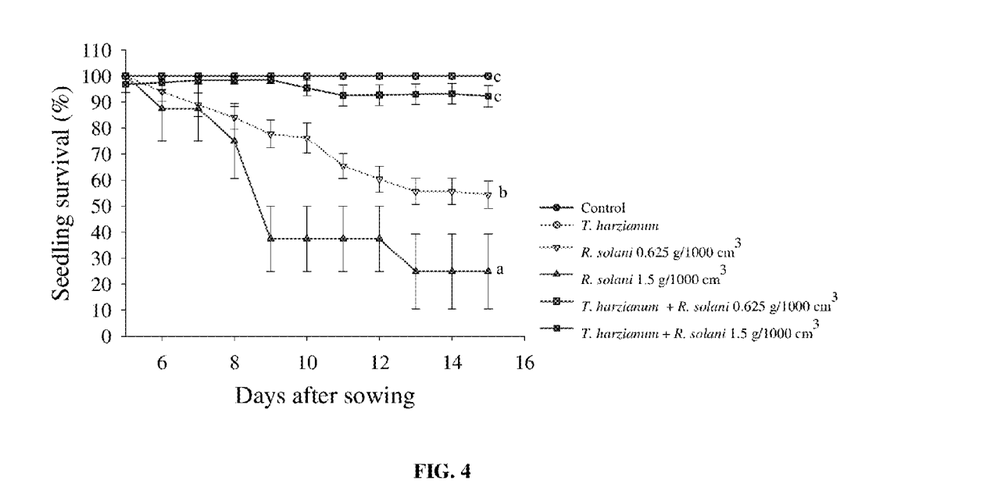
FIG. 4 is a graph depicting the probability of emerged seedlings surviving post-emergence damping-off for Cantaloupe melon (cv. 'Hales Best') sown in soil infested by *Rhizoctonia solani* applied at two rates (0.625 and 1.5 g/1000 cm$^3$) with or without biological treatment with *Trichoderma harzianum* T-22 (0.4 g MS granule/1000 cm$^3$) in growth chamber bioassays. Time censored for damping-off incidence up to 15 days after sowing. Values are means (±SE) of three independent experiments. Survival curves followed by different letters are statistically significant according to the log-rank test ($P \leq 0.05$). Curves for the control, *T. harzianum*, and *T. harzianum+R. solani* 0.625 g/1000 cm$^3$ overlap and are not significantly different from each other.

Treating potting mix with R. solani reduced the percentage of melon seeds that emerged and also resulted in delayed emergence compared to the negative control or seeds treated only with T. harzianum ($\chi^2_{(5)}$=44.37, P<0.0001). The higher inoculum rate of R. solani impaired seed germination to a greater extent compared to the other treatments. By contrast, the percent emergence of melon seedlings were significantly increased in the presence of the antagonist for the highest level of R. solani inoculum and arithmetically increased, though not significantly, for the treatment with the lower level of R. solani inoculum (Table 8). Disease reduction for treatments that combined R. solani and T. harzianum was calculated based on the disease levels obtained when seeds were grown in potting mix infested with the same rate of pathogen inoculum alone. Thus, the presence of T. harzianum microsclerotia substantially increased the proportion of healthy seedlings at day 15 ($\chi^2_{(5)}$=54.09, P<0.0001). The progression of damping-off over time was more pronounced in both treatments with only R. solani (log-rank test: $\chi^2_{(5)}$= 194.7, P<0.0001) (FIG. 4). By contrast, the antagonist reduced the level of post-emergence damping-off by 90 and 100%, respectively, compared to soil inoculated with the high and low level of R. solani only. Interestingly, the addition of T. harzianum microsclerotia granules to either inoculum level of R. solani significantly increased the likelihood of melon seedling survival to damping-off compared to the respective treatments without the antagonist. Seedlings with damping-off symptoms were confirmed to be infected with R. solani as revealed by the characteristic morphology of fungal growth from surface sterilized root and hypocotyl tissues plated on MRB agar (FIG. 5). Conversely, soil samples and surface sterilized root and stem fragments from potting mix treated with T. harzianum showed outgrowth of T. harzianum when plated on MRB, indicating that this biocontrol fungus maintained high populations in inoculated potting mix and was closely associated with plant root tissues (FIG. 5).

TABLE 8

Percentage of cantaloupe seeds that emerged and percentage that developed into healthy seedlings in growth chamber bioassays after treatments with Trichoderma harzianum T-22 (0.4 g formulated granule/1000 cm³) to control R. solani inoculated at two rates (0.563 and 1.5 g/1000 cm³) in non-sterile potting medium 15 days after sowing.

| Soil treatment | Total emergence (%)$^a$ | Healthy seedlings (%)$^c$ |
| --- | --- | --- |
| Control (no pathogen) | 84.3 a$^\dagger$ | 84.3 a |
| Control - T. harzianum | 84.3 a | 84.3 a |
| R. solani 0.625 g/L | 61.1 b | 33.3 c |
| R. solani 1.5 g/L | 11.1 c | 2.8 d |
| R. solani 0.625 g/L + T. harzianum | 75.9 ab | 75.9 ab |
| R. solani 1.5 g/L + T. harzianum | 63.9 b | 58.3 b |

$^a$Percentage of seedling emergence out of 18 seeds sown per punnet averaged across three independent experiments.
$^c$Percentage of 18 seeds that developed healthy seedlings averaged across three independent experiments.
$^\dagger$Means within a column that are not followed by the same letter are significantly different (P ≤ 0.05).

Example 5

Duel Production of Trichoderma harzianum T-22 Microsclerotia and Submerged Conidia Via Bioreactor Using the Trichoderma harzianum T-22 as disclosed above, microsclerotia, conidia, and biomass production were evaluated under a 5 L B. Braun fermentor, 4 L in volume. Using a basal salt medium supplemented with glucose and cottonseed flour to produce 30:1 C:N ratio and contained 36 g carbon L-1. Cultures of Trichoderma harzianum T-22 were grown for 4 days a 28° C. The reactor was set a 900 rpm impeller speed allowing for 1.5 L air per minute such that air flow maintains dissolved oxygen levels near or above zero and providing at least 0.1 $V_{air}/V_{culture\ media}$. Surprisingly, after four days of culture growth, aeration of the bioreactor allowed for improved yields of microsclerotia and improved yield of submerged conidia, as disclosed in Table 9. Additionally, as disclosed in Table 10, dried microsclerotia-diatomaceous earth formulations from the 5 L bioreactor yielded 5.3×10$^9$ conidia per gram when rehydrated and incubated on water agar. Also, 97% of the submerged conidia formed in this liquid fermentation were viable following air drying to less than 5% moisture.

TABLE 9

| Fermentation Method | Microsclerotia (×10$^6$ L$^{-1}$) | Biomass (g L$^{-1}$) | Submerged Conidia (×10$^{12}$ L$^{-1}$) |
| --- | --- | --- | --- |
| Shake Flask | 3.3 | 19.0 | 0.0 |
| Bioreactor | 10.8 | 29.9 | 1.9 |

TABLE 10

| Fungal Propagule Produced in Bioreactor | Conidia Production (conidia g$^{-1}$ dry formulate) | Viability (Germination) Before drying - After drying |
| --- | --- | --- |
| Microsclerotia | 5.3 × 10$^9$ | ND |
| Submerged Conidia | ND | 96%-93% |

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both".

When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the invention has been described with reference to details of the illustrated embodiment, these details are not intended to limit the scope of the invention as defined in the appended claims. All cited references and published patent applications cited in this application are incorporated herein by reference.

The embodiment of the invention in which exclusive property or privilege is claimed is defined as follows:

1. A composition comprising microsclerotia of a *Trichoderma* species with an agronomically acceptable carrier wherein said microsclerotia, upon rehydration, germinate hyphally or germinate sporogenically to produce conidia.

2. The composition of claim 1, wherein said *Trichoderma* species comprises *Trichoderma harzianum*.

3. The composition of claim 1, wherein said microsclerotia are present in an effective amount of control of a fungal plant disease.

4. The composition of claim 3, wherein the fungal plant disease is *Rhizoctonia, Sclerotinia, Sclerotiorum, Fusarium, Verticillium, Phytophthora, Castenea, Armillaria, Pythium,* or *Thielaviopsis*.

5. The composition of claim 1, wherein said microsclerotia are present in an effective amount to promote plant growth.

6. The composition of claim 1, wherein said microsclerotia are produced by liquid culture fermentation and are present in a recovered biomass in a concentration at least about $1 \times 10^5$ microsclerotia per gram of said biomass.

7. The composition of claim 1, wherein the fungal composition is combined with an agrochemical, biopesticide, pesticide, fungicide, microbe, biostimulant, or combinations thereof.

8. A method for producing a fungus containing a high concentration of desiccation tolerant fungal micro sclerotia, comprising: a) inoculating a liquid culture medium comprising a carbon source and a nitrogen source with fungal propagules of a biocontrol fungus comprising a hyphae or spores of a *Trichoderma* species, said nitrogen source having a concentration between 8 grams/liter and 40 grams/liter and said carbon source having a concentration greater than 40 grams/liter; b) incubating the propagules for a sufficient time to allow for production of microsclerotia; and c) collecting the resulting microsclerotia.

9. The method of claim 8, wherein the resulting microsclerotia are storage stable after being dried.

10. The method of claim 8, wherein the resulting microsclerotia are applied to seeds.

11. The method of claim 8, wherein the resulting microsclerotia upon rehydration, produces conidia.

12. A method for producing a fungus containing a high concentration of desiccation tolerant fungal micro sclerotia and submerged conidia, comprising: a) inoculating a liquid culture medium comprising a carbon source and a nitrogen source with fungal propagules of a fungus comprising hyphae or spores of a *Trichoderma* species, said nitrogen source having a concentration between 8 grams/liter and 40 grams/liter and said carbon source having a concentration greater than 40 grams/liter; b) incubating the propagules in a bioreactor for a sufficient time to allow for production of microsclerotia and submerged conidia c) aerating the bioreactor to an air flow that maintains dissolved oxygen levels near or above zero and providing at least $0.1 V_{air}/V_{culture\ media}$; and d) collecting the resulting microsclerotia and submerged conidia.

13. The method of claim 12, wherein about $10.8 \times 10^6$ microsclerotia per liter and about $1.9 \times 10^{12}$ submerged conidia per liter is collected.

* * * * *